(12) United States Patent
Hong

(10) Patent No.: US 6,955,139 B2
(45) Date of Patent: Oct. 18, 2005

(54) TAIL SUSPENSION TEST APPARATUS

(75) Inventor: Chen-Jee Hong, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 19 days.

(21) Appl. No.: 10/742,005

(22) Filed: Dec. 18, 2003

(65) Prior Publication Data

US 2004/0143414 A1 Jul. 22, 2004

(30) Foreign Application Priority Data

Jan. 17, 2003 (TW) ............................... 92101057 A

(51) Int. Cl.$^7$ .......................................... A01K 13/00
(52) U.S. Cl. ..................................... 119/809; 119/421
(58) Field of Search ........................ 119/809, 417, 421; 702/150; 435/808; 340/573.1, 573.3; 239/530, 239/565, 566, 567, 568

(56) References Cited

U.S. PATENT DOCUMENTS

| | | | |
|---|---|---|---|
| 3,897,751 A * | 8/1975 | Gullino et al. .............. 119/420 |
| 4,971,117 A * | 11/1990 | Hendrickson ................. 138/41 |
| 5,608,209 A * | 3/1997 | Matsuda ....................... 250/221 |
| 5,816,256 A * | 10/1998 | Kissinger et al. ........... 128/897 |
| 5,832,878 A * | 11/1998 | Bonsall et al. .............. 119/769 |
| 6,047,249 A * | 4/2000 | Piernot et al. ............... 702/150 |
| 6,078,876 A * | 6/2000 | Rosenberg et al. ......... 702/152 |
| 6,279,511 B1 * | 8/2001 | Loughnane ................. 119/769 |
| 6,697,760 B2 * | 2/2004 | Myers ......................... 702/150 |
| 6,715,444 B1 * | 4/2004 | Yabusaki et al. ........... 119/421 |
| 6,789,510 B1 * | 9/2004 | Lee ............................. 119/811 |
| 6,799,535 B2 * | 10/2004 | Hong .......................... 119/421 |
| 2002/0183961 A1 * | 12/2002 | French et al. ............... 702/150 |
| 2004/0006280 A1 * | 1/2004 | Geddes et al. .............. 600/509 M |

* cited by examiner
M

Primary Examiner—Yvonne R. Abbott
(74) Attorney, Agent, or Firm—Haverstock & Owens LLP

(57) ABSTRACT

The tail suspension test apparatus for detecting a struggling state of an animal by suspending a tail of the animal includes an optical mouse, an opaque piece located within a sensing range of the optical mouse, and a fixing device connected with the opaque piece for fixing the tail of the animal. When the animal is struggling, an action of the opaque piece is induced and detected by the optical mouse.

12 Claims, 5 Drawing Sheets

TAIL SUSPENSION TEST APPARATUS

FIELD OF THE INVENTION

This invention relates to a tail suspension test apparatus, and more particularly to a tail suspension test apparatus using an optical mouse for detection.

BACKGROUND OF THE INVENTION

Tail suspension test (TST), which is invented by Steru et al. in 1985, is used for determining whether a mouse has melancholia or depression. The test is to suspend the tail of the mouse and then detect the agitation and immobility times of the mouse in a specific time (6 minutes in general). Many studies have proven that the immobility time of the depressed mouse is longer, since the depressed mouse is easily disappointed and gives up struggling. Such situation can be improved by treating the mouse with antidepressant drugs. Therefore, TST is a common method for screening antidepressant drugs, so as to develop new antidepressant drugs.

The advantage of TST is easy to perform, but the disadvantage thereof is that it is hard to define by naked eyes whether the action is agitation or immobility for those small actions between agitation and immobility, so that the variation and error of the experiments increase. To overcome this problem, Steru et al. used a digital-tension meter in 1987 to detect the struggling force of the mouse in each time point and connect to a computer to form an automatic detector (ITEMATIC-TST). However, such detector can only detect the tension change in the vertical direction but cannot detect the swing action in the horizontal direction, so that it is not widely used. In 1992, a Japanese named Nomura S used photoelectric elements and a microangular potentiometer to detect the struggling of the mouse, and then convert the predetermined analog potential signals into digital signals. However, such apparatus is complicated and inconvenient to operate, and many actions of the mouse cannot be detected; besides, it is too expensive, so this apparatus has not been used in any published paper. Thus, at present, when using TST to evaluate the melancholia or depressive symptom of the mouse, it is still observed by naked eyes and counted time by hand, which causes error easily.

Therefore, the present invention provides a TST apparatus which overcomes the above-mentioned disadvantages.

SUMMARY OF THE INVENTION

It is an object of the present invention to provide a tail suspension test (TST) apparatus using an optical mouse for detection, which can easily and precisely detect the struggling state of the animal.

In accordance with an aspect of the present invention, the tail suspension test (TST) apparatus for detecting a struggling state of an animal by suspending a tail of the animal includes an optical mouse, an opaque piece located within a sensing range of the optical mouse, and a fixing device connected with the opaque piece for fixing the tail of the animal. When the animal is struggling, an action of the opaque piece is induced and detected by the optical mouse.

Preferably, the device further includes a base for vertically fixing the optical mouse.

Preferably, the device further includes a spring having a first end fixed on the base and a second end connected with the opaque piece.

Preferably, the opaque piece is located between the base and the optical mouse.

Preferably, the opaque piece is one of a plastic piece and an aluminum piece.

Preferably, the fixing device comprises a tape for adhering the tail of the animal.

Preferably, the fixing device comprises a clip for fixing the tape and the opaque piece.

Preferably, the optical mouse is connected to a computer to record a movement of the animal during struggling by a coordinate displacement of the optical mouse.

Preferably, the movement comprises both vertical and horizontal directions.

Preferably, the computer comprises a software for counting agitation time and immobility time of the animal.

Preferably, the animal is a mouse.

In accordance with another aspect of the present invention, the tail suspension test (TST) device for detecting a struggling state of an animal by suspending a tail of the animal includes a base vertical to the horizontal plane, an optical mouse fixed on the base, a spring having a first end fixed on the base and a second end, an opaque piece located between the base and the optical mouse and connected with the second end of the spring, and a fixing device connected with the opaque piece for fixing the tail of the animal. When the animal is struggling, an action of the opaque piece is induced and detected by the optical mouse.

Preferably, the opaque piece is one of a plastic piece and an aluminum piece.

Preferably, the fixing device comprises a tape for adhering the tail of the animal.

Preferably, the fixing device comprises a clip for fixing the tape and the opaque piece.

Preferably, the optical mouse is connected to a computer to record a movement of the animal during struggling by a coordinate displacement of the optical mouse.

Preferably, the movement comprises both vertical and horizontal directions.

Preferably, the computer comprises a software for counting agitation time and immobility time of the animal.

Preferably, the animal is a mouse.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

Figure 1:
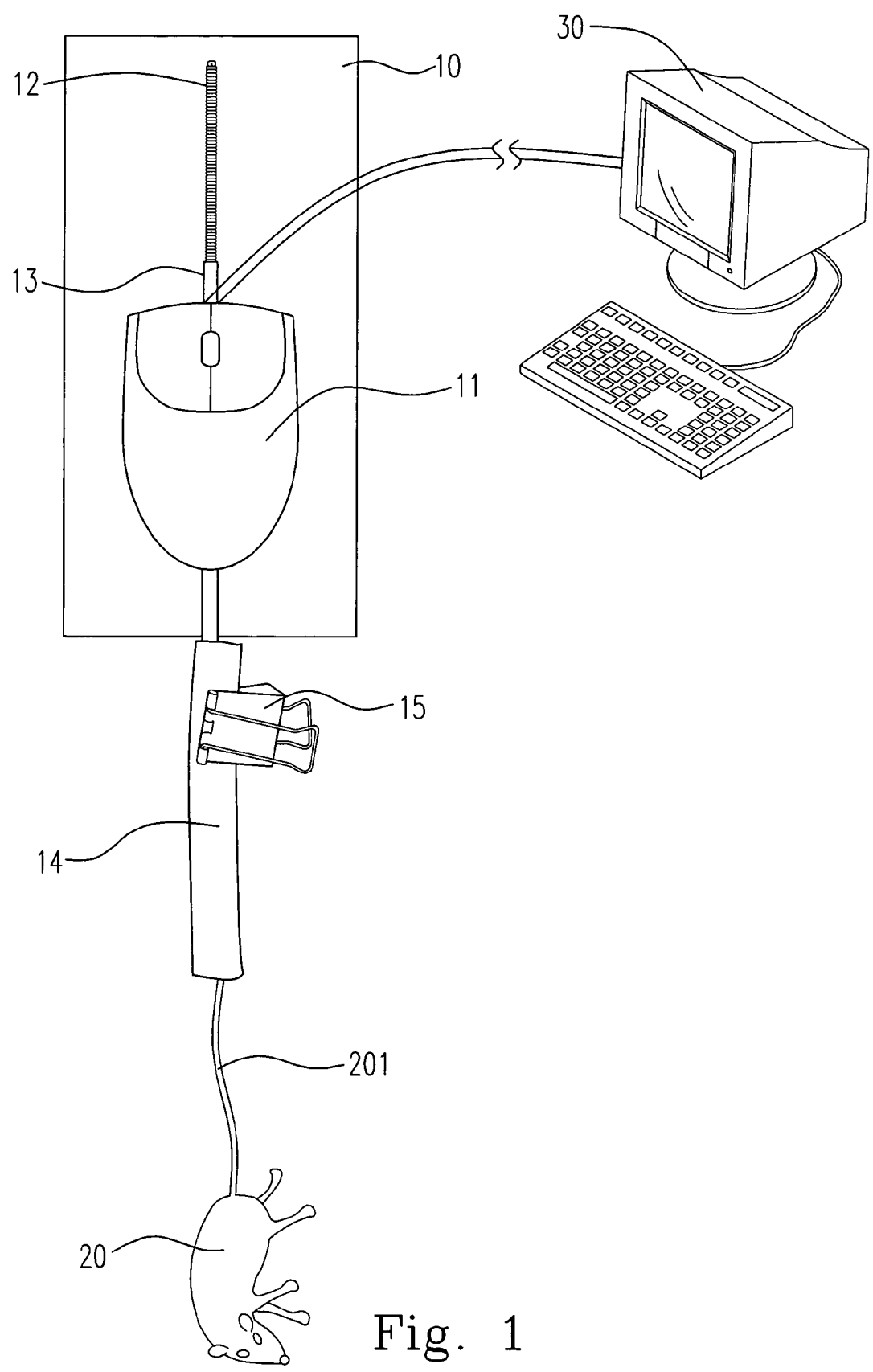
FIG. 1 shows the tail suspension test apparatus according to the preferred embodiment of the present invention.

Please refer to FIG. 1 showing the tail suspension test apparatus according to the preferred embodiment of the present invention, in which a mouse is suspended thereon for illustration. The main idea of the present invention is to use an optical mouse to detect the struggling state of the mouse in the tail suspension test. According to this idea, a flat space is formed under the bottom of the optical mouse. The space is within the sensing range of the optical mouse and it allows a thin film on which the mouse is suspended to freely slide up and down and left and right therein during the struggling of the mouse, and to be detected by the optical mouse. The tail suspension test apparatus of the present invention is further illustrated in detail in the following descriptions.

Figure 2:
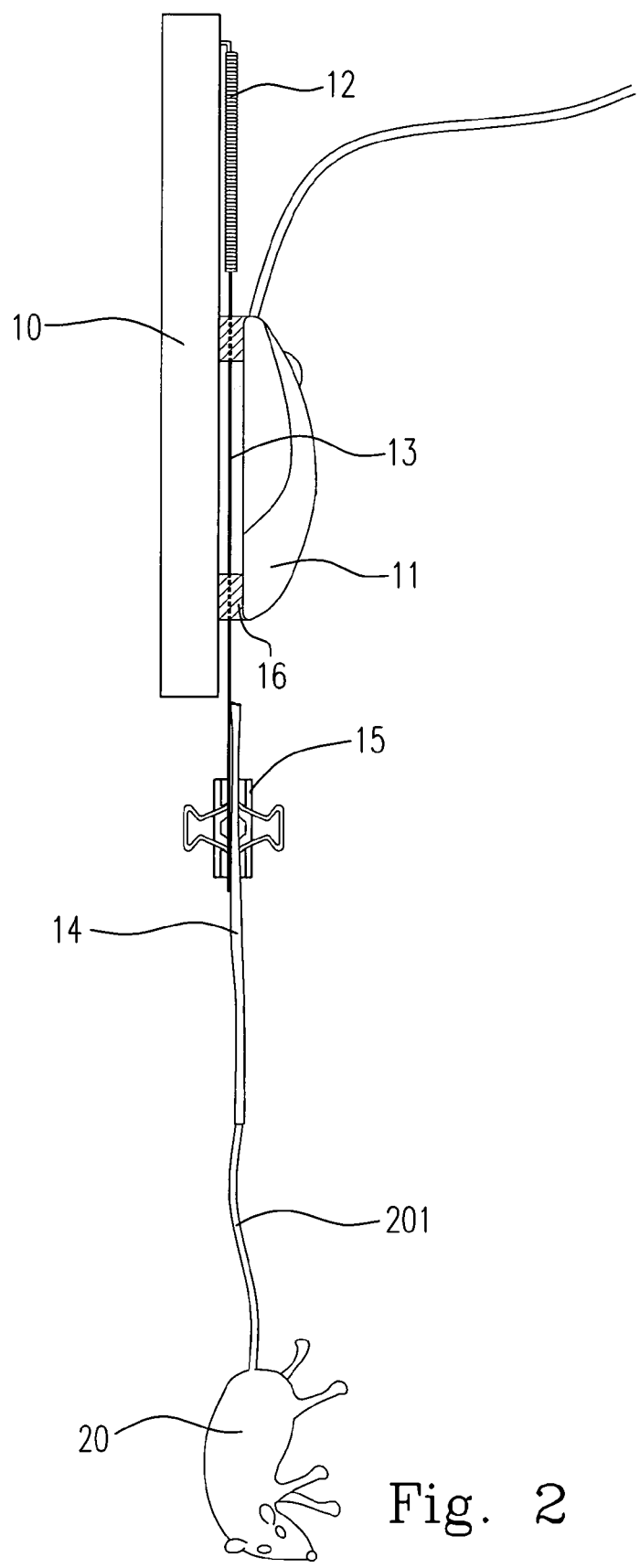
FIG. 2 is a side view of the tail suspension test apparatus in FIG. 1.

As shown in FIG. 1, the tail suspension test apparatus includes a base 10 which is set to be vertical to the horizontal plane, and an optical mouse 11 fixed on the base 10, in which the optical mouse can be properly modified and adhered to the base 10 by double-coated form tapes 16 (as shown in FIG. 2). The tail suspension test apparatus further includes a spring 12 having an upper end fixed on the base 10 and a lower end connected with a thin film. The thin film is an opaque piece 13, such as a plastic piece or an aluminum piece, and can pass through the bottom space formed between the optical mouse 11 and the base 10 (as shown in FIG. 2). The opaque piece 13 can freely slide up and down and left and right in the sensing range of the optical mouse 11. The lower end of the opaque piece 13, which passes through the bottom of the optical mouse 11, is used for suspending the tail 201 of the mouse 20 by a fixing device. The fixing device includes a tape 14 and a clip 15. The lower end of the tape 14 can adhere to the tail 210 of the mouse 20, and the upper end of the tape 14 can adhere to the opaque piece 13 and can be further fixed by the clip 15.

In addition, the tail suspension test apparatus can further include a blocking board (not shown) having an opening at the center, which can be put around the beginning of the tail to prevent the mouse from climbing up and out of suspension state that would interrupt the observation of the struggling of the mouse.

When the mouse 20 is suspended on the tail suspension test apparatus of the present invention, the struggling of the mouse 20 would induce the sliding of the opaque piece 13 to be detected by the optical mouse 11. The sliding of the opaque piece 13 would be converted into the coordinate displacement of the optical mouse 13 and recorded in the computer 30 which connects with the optical mouse 13. The computer 30 has a software for counting agitation time and immobility time of the mouse 20.

Figure 3:
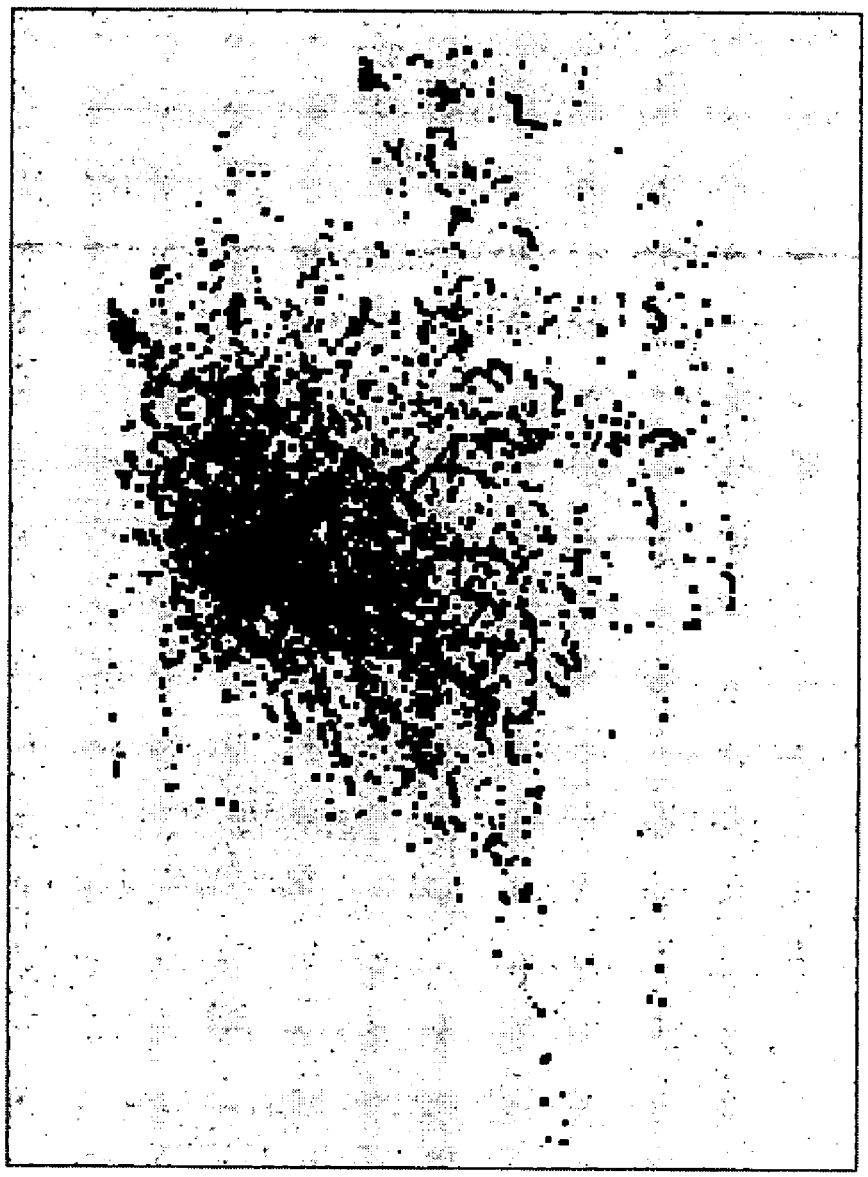
FIG. 3 is a scatter plot of the coordinate of the optical mouse recorded by the computer when the mouse is struggling.
Figure 4:
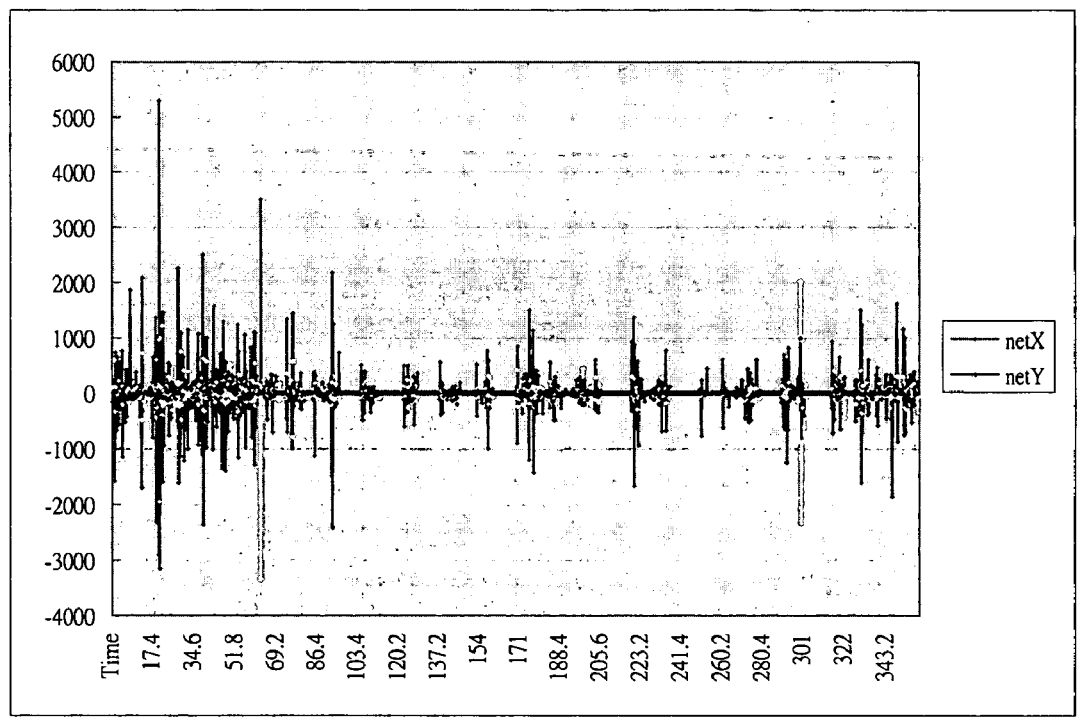
FIG. 4 is a broken line graph with the time as X axis and the speed of the coordinate displacement as Y axis.

According to the preferred embodiment, the present invention includes a software program, which is written by Visual Basic Language. The program is only 40 Kb, and can be operated in the operating environment of Windows 98 or advanced. The main functions of the program are recording the coordinates of the optical mouse in a constant period of time (0.05 sec~unlimited time), comparing the recorded coordinates in a constant times (2 times~unlimited times) and returning to zero, automatically calculating the speed of the coordinate displacement, and automatically counting the time of which the speed of the coordinate displacement is greater than the predetermined speed. The program can present each recorded coordinate during the experiment in a scatter plot (as shown in FIG. 3), so that the experimentalist can observe the struggling of the mouse directly. Moreover, the program can record all the data into Excel format, so that the experimentalist can use the drafting tools of Excel to plot the broken line graph with the time as X axis and the speed of the coordinate displacement as Y axis (as shown in FIG. 4). In addition, the program has a design about "Shift" key. When the "Shift" key is pressed, the struggling of the mouse can be recorded in an independent column of Excel; when the "Shift" key is released, the recording is stopped. Such design can help the experimentalist find the meaningful threshold for the struggling of the mouse.

Figure 5:
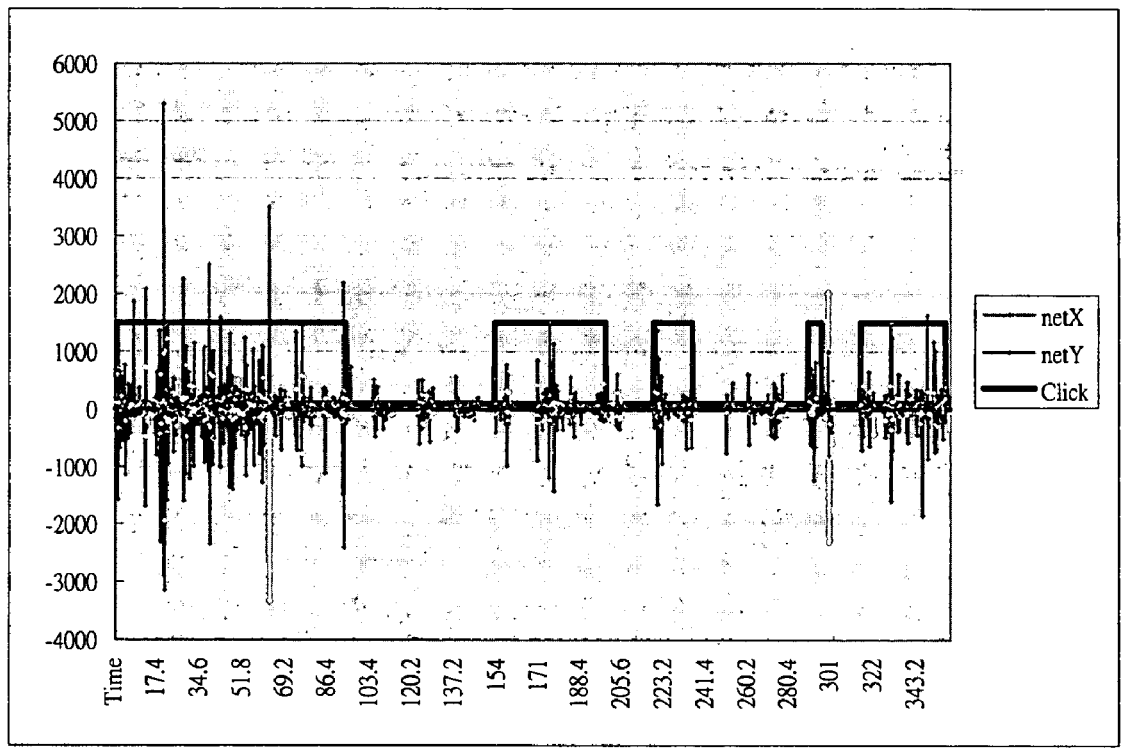
FIG. 5 is a broken line graph when the "shift" key is pressed during the experiment for comparing the automatic detection and the manual detection.

The operating procedures for the tail suspension test apparatus of the present invention are illustrated as follows:

1. The program is started, and the test time (sec), time interval for recoding the coordinates, correction frequency of the origin, thresholds for detecting tiny action and significant action, number of the mouse, weight of the mouse, and other descriptions are set according to the needs.
2. The tail suspension test apparatus is set up, and the optical mouse is connected with the computer via the USB terminal, and then the opaque piece is pulled to make sure that the indication of the optical mouse moves with the movement of the opaque piece.
3. The mouse is adhered to one end of the tape, and the other end of the tape is fixed on the opaque piece by a clip. When the mouse is suspended, the "Enter" key is pressed to start to count time and detect.
4. During the experiment, each recorded coordinate is presented on the screen of the computer as a scatter plot, so that the experimentalist can observe the struggling of the mouse directly. For comparing a certain action observed by naked eyes with the data recorded by the program, the "Shift" key can be pressed, when observing the action, until the action disappears. There is a column used to record the numeral if the "Shift" key is pressed. When the "Shift" key is pressed in any time point (generally 0.2 or 0.3 sec), the numeral is recorded as 1500, otherwise is 0. In such way, the automatic detection and the manual detection can be compared on the broken line graph (as shown in FIG. 5).
5. When the detection is over, all the detected data are re-stored into ".csv" format, and can be opened, calculated, analyzed and drafted with Excel software. The times (sec) of the significant struggling, tiny struggling and immobility of the mouse during the suspension are counted according to the thresholds set before the experiment, and then the experiment is over.

In conclusion, the tail suspension test apparatus of the present invention uses an optical mouse for detection and has the following advantages:

1. The struggling of the mouse can be detected precisely and quantified to avoid the error due to the observation by naked eyes.
2. The struggling in both vertical and horizontal directions can be detected simultaneously.
3. The apparatus is simple and convenient, and the cost is low, so that apparatus is suitable for use in each laboratory.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A tail suspension test (TST) apparatus for detecting a struggling state of an animal by suspending a tail of said animal, comprising:
    an optical mouse;
    an opaque piece located within a sensing range of said optical mouse;
    a fixing device connected with said opaque piece for fixing said tail of said animal; and a base for vertically fixing said optical mouse, wherein when said animal is struggling, an action of said opaque piece is induced and detected by said optical mouse.

2. The device according to claim 1 further comprising a spring having a first end fixed on said base and a second end connected with said opaque piece.

3. The device according to claim 1 wherein said opaque piece is located between said base and said optical mouse.

4. A tail suspension test (TST) device for detecting a struggling state of an animal by suspending a tail of said animal, comprising:

a base vertical to the horizontal plane;

an optical mouse fixed on said base;

a spring having a first end fixed on said base and a second end;

an opaque piece located between said base and said optical mouse and connected with said second end of said spring; and a fixing device connected with said opaque piece for fixing said tail of said animal;

wherein when said animal is struggling, an action of said opaque piece is induced and detected by said optical mouse.

5. The device according to claim 4 wherein said opaque piece is one of a plastic piece and an aluminum piece.

6. The device according to claim 4 wherein said fixing device comprises a tape for adhering said tail of said animal.

7. The device according to claim 6 wherein said fixing device comprises a clip for fixing said tape and said opaque piece.

8. The device according to claim 4 wherein said optical mouse is connected to a computer to record a movement of said animal during struggling by a coordinate displacement of said optical mouse.

9. The device according to claim 8 wherein said movement comprises both vertical and horizontal directions.

10. The device according to claim 8 wherein said computer comprises a software for counting agitation time and immobility time of said animal.

11. The device according to claim 4 wherein said animal is a mouse.

12. A tail suspension test (TST) apparatus for detecting a struggling state of an animal by suspending a tail of said animal, comprising:

an optical mouse;

an opaque piece located within a sensing range of said optical mouse; and a fixing device connected with said opaque piece for fixing said tail of said animal;

wherein when said animal is struggling, an action of said opaque piece is induced and detected by said optical mouse, said optical mouse is connected to a computer to record a movement of said animal during struggling, by a coordinate displacement of said optical mouse, and said computer comprises a software for counting agitation time and immobility time of said animal.

* * * * *